(12) United States Patent
Hyodo et al.

(10) Patent No.: US 8,610,426 B2
(45) Date of Patent: Dec. 17, 2013

(54) CARBURIZATION SENSING METHOD (75) Inventors: Shigetoshi Hyodo, Osaka (JP);
Yoshikazu Takimoto, Osaka (JP);
Kazufumi Miyoshi, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 300 days.

(21) Appl. No.: 13/215,285

(22) Filed: Aug. 23, 2011

(65) Prior Publication Data
US 2012/0032672 A1    Feb. 9, 2012

Related U.S. Application Data (63) Continuation of application No. PCT/JP2010/052147, filed on Feb. 15, 2010.

(30) Foreign Application Priority Data

Feb. 25, 2009  (JP) .................................. 2009-042535

(51) Int. Cl.
*G01N 27/72*    (2006.01)

(52) U.S. Cl.
USPC ........................................................ 324/239

(58) Field of Classification Search
USPC ........................................................ 324/239
See application file for complete search history.

(56) References Cited

FOREIGN PATENT DOCUMENTS

| JP | 03-253555   | 11/1991 |
|----|-------------|---------|
| JP | 04-145358   | 5/1992  |
| JP | 06-88807    | 3/1994  |
| JP | 62-6153     | 7/1994  |
| JP | 2000-266727 | 9/2000  |
| JP | 2004-279054 | 10/2004 |
| JP | 2004-279055 | 10/2004 |
| JP | 2009-26682  | 2/2009  |

*Primary Examiner* — Reena Aurora
(74) *Attorney, Agent, or Firm* — Clark & Brody (57) ABSTRACT

A carburization sensing method according to the present invention includes: a first procedure of attaching a magnetic material to a reference material which has equivalent electromagnetic properties to those of a test material and is not carburized, a second procedure of measuring magnetic strength of each magnetic material and to acquire an electromagnetic test output value for each magnetic material, a third procedure of calculating a correlation between the measured magnetic strength value and the electromagnetic test output value, a fourth procedure of measuring magnetic strengths on a plurality of carburized materials, a fifth procedure of calculating a correlation between a carburized depth and the measured magnetic strength value, a sixth procedure of determining a threshold value Th2 of the measured magnetic strength value corresponding to a threshold value Th1 of the carburized depth to be sensed, a seventh procedure of determining a threshold value Th3 of an electromagnetic test output value corresponding to the threshold value Th2 of the measured magnetic strength value, and an eighth procedure to sense whether carburization occurs or not in a test material based on the magnitude correlation between the electromagnetic test output value of the test material and the threshold value Th3 of the electromagnetic test output value.

4 Claims, 5 Drawing Sheets

CARBURIZATION SENSING METHOD

TECHNICAL FIELD

The present invention relates to a method for sensing whether carburization occurs or not in a test material such as a steel pipe or tube by an electromagnetic testing such as an electromagnetic induction testing and a magnetic flux leakage testing. In particular, the present invention relates to a method with which a threshold value of an electromagnetic test output value, which corresponds to a threshold value of a carburized depth to be sensed, can be accurately determined and thereby it is possible to accurately sense whether carburization occurs or not.

BACKGROUND ART

It is known that among various steel materials, austenitic stainless steel is susceptible to carburization. For example, a cracking tube, which is used for the thermal decomposition reaction in an ethylene manufacturing process of a petrochemical plant, is made of austenitic stainless steel, and carburization occurs on its inner surface after being used for long hours. Moreover, in the manufacturing process of the cracking tube, carburization occurs when heat treatment is performed in a poorly degreased condition. Since the occurrence of such carburization may cause a significant reduction of the life of the cracking tube, there is a need for accurately sensing whether carburization occurs or not.

For this reason, conventionally, an electromagnetic test such as an electromagnetic induction test is carried out on a cracking tube installed in a plant as a nondestructive inspection across the entire length of the cracking tube at the time of periodic maintenance of the plant so that whether carburization occurs or not is sensed based on the magnitude of the output value thereof. Moreover, also in the manufacturing process of cracking tube, whether carburization occurs or not is sensed by performing an electromagnetic test across its entire length or by cutting off both ends thereof and performing a microstructure observation.

In the above described electromagnetic test, it is a general practice that using a calculated calibration curve, which is a previously calculated correspondence between a carburized depth and an electromagnetic test output value, a threshold value of the electromagnetic test output value corresponding to a threshold value of the carburized depth to be sensed is determined in advance. Then, whether carburization occurs or not in a test material is sensed based on a magnitude correlation between the electromagnetic test output value obtained by performing the electromagnetic test on the test material and the threshold value of the electromagnetic test output value which is predetermined as described above.

In general, when calculating the above described calibration curve, first, a plurality of carburized materials each of which is expected to have a different carburized depth are prepared, and each carburized material is subjected to an electromagnetic test to obtain an electromagnetic test output value. Thereafter, each carburized material is cut off and subjected to microstructure observation so that an actual carburized depth of each carburized material, from which the electromagnetic test output value has been acquired, is measured. Thereby, it is possible to calculate a calibration curve which is a correspondence between the carburized depth and the electromagnetic test output value.

In this situation, since the carburized depth is affected by the manufacturing history or the usage history of a cracking tube, a plurality of carburized materials collected from one cracking tube having the same history may have an equivalent carburized depth. In other words, a plurality of carburized materials each having a different carburized depth may not necessarily be collected from one cracking tube conveniently to calculate the above described calibration curve. Therefore, it is a general practice that to increase the possibility to collect carburized materials having different carburized depths, carburized materials are collected respectively from a plurality of cracking tubes, each of which has a different history such as a manufacturing lot and a usage time, and are subjected to the calculation of the calibration curve.

As describe above, each carburized material to be subjected to the calculation of calibration curve is collected from the respective ones of a plurality of cracking tubes having different histories. Therefore, even if a plurality of cracking tubes having the same constituents and dimensions (outer diameter and inner diameter) in terms of the design specification are selected, and each carburized material is collected from each of the cracking tubes, the constituents and the dimension of the base metal of each carburized material may vary. As a result, the electromagnetic properties (electric resistance, etc.) of the base metal of each carburized material may vary.

In an electromagnetic testing such as an electromagnetic induction testing, it is a general practice that an alternating current of from several hundreds of Hz to several tens of kHz is applied depending on the wall thickness of the material to be measured such that the penetration depth of the alternating current is several times of the wall thickness. Therefore, even assuming that carburization has not occurred in each carburized material, the different electromagnetic properties of the base metal of each carburized material lead to a different electromagnetic test output value of each carburized material. That is, the electromagnetic test output value when the carburized depth is 0 μm (the reference point) will vary from one carburized material to another. Thus, the accuracy of the calibration curve, which is calculated by using the electromagnetic test output values for which the reference point varies from one carburized material to another, will be reduced according to the amount of deviation of each reference point. As a result, a problem arises in that the accuracy of the threshold value of the electromagnetic test output value, which is predetermined by using the calibration curve as described above, will also be reduced, further leading to a decline of accuracy in sensing whether carburization occurs or not.

Although various methods for sensing whether carburization occurs or not have been proposed including ones which are not in the actual use yet (for example, see JP3-253555A, JP62-6153A, JP4-145358A, JP6-88807A, JP2000-266727A, JP2004-279054A, and JP2004-279055A), none of these method is able to solve the above described problems.

SUMMARY OF INVENTION

The present invention has been made in view of the above described prior arts, and has its object to provide a carburization sensing method with which a threshold value of an electromagnetic test output value corresponding to a threshold value of a carburized depth to be sensed can accurately be determined, and thereby whether carburization occurs or not can accurately be sensed.

In order to solve the above described problems, the present invention is a method for sensing whether carburization occurs or not in a test material by an electromagnetic test, the method being characterized by including the following first to eighth procedures.

(1) First Procedure

A material which has equivalent electromagnetic properties to those of a test material and is not carburized is selected as a reference material, and at least three magnetic materials each having a different magnetic strength are attached to a target surface for carburization sensing of the reference material.

(2) Second Procedure

The magnetic strength of each magnetic material which is attached to the reference material in the above described first procedure is measured, and an electromagnetic test is performed on the above described each magnetic material to acquire an output value thereof.

(3) Third Procedure

Based on the measured magnetic strength values and the electromagnetic test output values of the each magnetic material, which are obtained in the second procedure, a correspondence between the measured magnetic strength value and the electromagnetic test output value is calculated.

(4) Fourth Procedure

The magnetic strength is measured on a plurality of carburized materials each having a different carburized depth.

(5) Fifth Procedure

Based on the carburized depths and the measured magnetic strength values of the each carburized material obtained in the fourth procedure, a correspondence between the carburized depth and the measured magnetic strength value is calculated.

(6) Sixth Procedure

Based on the correspondence between the carburized depth and the measured magnetic strength value obtained in the fifth procedure, a threshold value of the measured magnetic strength value corresponding to a threshold value of a carburized depth to be sensed is determined.

(7) Seventh Procedure

Based on the correspondence between the measured magnetic strength value and the electromagnetic test output value obtained in the third procedure, a threshold value of the electromagnetic test output value corresponding to the threshold value of the measured magnetic strength value determined in the sixth procedure is determined.

(8) Eighth Procedure

Whether carburization occurs or not in the test material is sensed based on a magnitude correlation between the electromagnetic test output value obtained by performing the electromagnetic test on the test material, and the threshold value of the electromagnetic test output value determined in the seventh procedure.

According to the present invention, a correspondence between the measured magnetic strength value and the electromagnetic test output value is calculated by performing the first to the third procedures. Here, "magnetic strength" as used in the present invention has a positive correlation with the amount of ferrite (the area ratio of ferrite structure), which is generally measured by using a ferrite meter. This ferrite meter is an instrument to measure the amount of ferrite by applying an ultra-low frequency (less than 100 Hz) alternating magnetic field to the material to be measured and taking advantage of the fact that magnetic induction increases with ferrite included in the material to be measured. Therefore, in the second procedure, when measuring the magnetic strength of each magnetic material attached to the reference material, using a ferrite meter which applies an alternating magnetic field of ultra-low frequency thereto will result in a measured magnetic strength value which is less likely to be affected by the electromagnetic properties of the part of the reference material at which each magnetic material is attached.

On the other hand, in the second procedure, the electromagnetic test output value obtained by performing electromagnetic test on each magnetic material attached to the reference material is likely to be affected by the electromagnetic properties of the part of the reference material to which each magnetic material is attached, since, as described above, a high frequency alternating magnetic field is applied in the electromagnetic test. In this way, although the electromagnetic test output value of each magnetic material is affected by the electromagnetic properties of the part of the reference material to which each magnetic material is attached, since each magnetic material is attached to a single reference material, its effect is uniform and is not likely to vary among electromagnetic test output values of each magnetic material. Moreover, since the reference material has equivalent electromagnetic properties to those of the test material (the base metal of the test material), the electromagnetic test output value of each magnetic material is affected to an equivalent degree as in the case where the test material is subjected to an electromagnetic test. That is, the reference points of the electromagnetic test output values of the respective magnetic materials are substantially equal to each other, and also substantially coincide with the reference point of electromagnetic test output value of the test material.

Therefore, in a correspondence between the measured magnetic strength value obtained by performing the first to third procedures and the electromagnetic test output value, although the electromagnetic test output value is affected by the electromagnetic properties of the reference material (electromagnetic properties of the test material), the reference point thereof stays substantially fixed.

Further, according to the present invention, by performing the fourth and fifth procedures, a correspondence between the carburized depth and the measured magnetic strength value is calculated. Here, for example, "carburized depth" as used in the present invention can be measured by cutting off each carburized material and performing microstructure observation after measuring the magnetic strength, and will not be affected by the electromagnetic properties of the base metal of each carburized material.

On the other hand, in the fourth procedure, when measuring the magnetic strength of each carburized material, if a ferrite meter that applies an ultra-low frequency alternating magnetic field is used, the measured magnetic strength value thereof is not likely to be affected by the electromagnetic properties of the base metal of each carburized material.

Therefore, the correspondence between the carburized depth and the measured magnetic strength value obtained by performing the fourth and fifth procedures is not likely to be affected by the electromagnetic properties of the base metal of each carburized material, and thus by the electromagnetic properties of the test material (the base metal of the test material).

Further, according to the present invention, a threshold value of the measured magnetic strength value corresponding to a threshold value of the carburized depth to be sensed is determined by performing the sixth procedure, and a threshold value of the electromagnetic test output value corresponding to the threshold value of the measured magnetic strength value, which is determined as described above, is determined by performing the seventh procedure. That is, consequently, a threshold value of the electromagnetic test output value corresponding to a threshold value of the carburized depth to be sensed is determined in a same fashion as in prior arts by performing the sixth and seventh procedures.

In the present invention, however, in contrast to prior arts, first, in the sixth procedure, a threshold value of the measured magnetic strength value corresponding to a threshold value of the carburized depth to be sensed is determined based on the correspondence between the carburized depth and the measured magnetic strength value obtained in the fifth procedure. Since the correspondence between the carburized depth and the measured magnetic strength value obtained by the fifth procedure is less likely to be affected by the electromagnetic properties of the test material as described above, it is possible to accurately determine a threshold value of the measured magnetic strength value corresponding to the threshold value of the carburized depth to be sensed. Then, in the seventh procedure, a threshold value of the electromagnetic test output value corresponding to the threshold value of the measured magnetic strength value determined in the sixth procedure is determined based on the correspondence between the measured magnetic strength value and the electromagnetic test output value obtained in the third procedure. In the correspondence between the measured magnetic strength value and the electromagnetic test output value obtained in the third procedure, as described above, although the electromagnetic test output value is affected by the electromagnetic properties of the test material, since its reference point stays substantially fixed, it is possible to accurately determine a threshold value of the electromagnetic test output value corresponding to a threshold value of the measured magnetic strength value.

Therefore, in the present invention, by performing the sixth and seventh procedures, it is possible, in contrast to prior arts, to accurately determine a threshold value of the electromagnetic test output value corresponding to a threshold value of the carburized depth to be sensed.

After performing the first to the seventh procedures, in the eighth procedure, by sensing whether carburization occurs or not in the test material based on the magnitude correlation between the electromagnetic test output value obtained by performing the electromagnetic test on the test material and the threshold value of the electromagnetic test output value determined in the seventh procedure, it is possible to improve the sensing accuracy.

It is noted that in the present invention, the first to the eighth procedures need not necessarily be performed in this order, and for example, it is also possible to first perform the fourth and the fifth procedures, and then to perform the first to the third procedures.

In the above described first procedure, for example, any one of a magnetic tape, a ferrite core which is inserted into a solenoid coil used for electronic parts and flaw inspection, a cut out specimen of a magnetic metal material such as iron may be attached to the above descried reference material as the magnetic material.

Further, in the above described second and eighth procedures, it is possible to perform an electromagnetic test by using a sensor that outputs an absolute value signal or a sensor that outputs a differential signal.

The sensor that outputs an absolute value signal may be exemplified by, for example, a configuration that includes a single detection coil disposed near the test material and outputs a detection signal at the detection coil, and a configuration that includes a pair of detection coils, one of which is disposed near the test material and the other is disposed near an object that serves as a standard, and outputs a difference of detection signals at each detection coil. Moreover, the sensor that outputs a differential signal may be exemplified by, for example, a configuration that includes a pair of detection coils disposed near the test material and outputs a difference between detection signals at each detection coil.

As so far described, according to the carburization sensing method relating to the present invention, it is possible to accurately determine a threshold value of the electromagnetic test output value corresponding to a threshold value of the carburized depth to be sensed, and thereby accurately sense whether carburization occurs or not.

DESCRIPTION OF EMBODIMENTS

Hereafter, referring to the appended drawings, embodiments of the present invention will be described taking an example of a case in which the test material a steel tube, and an eddy current test is performed as the electromagnetic test.
<First Embodiment>

Figure 1:
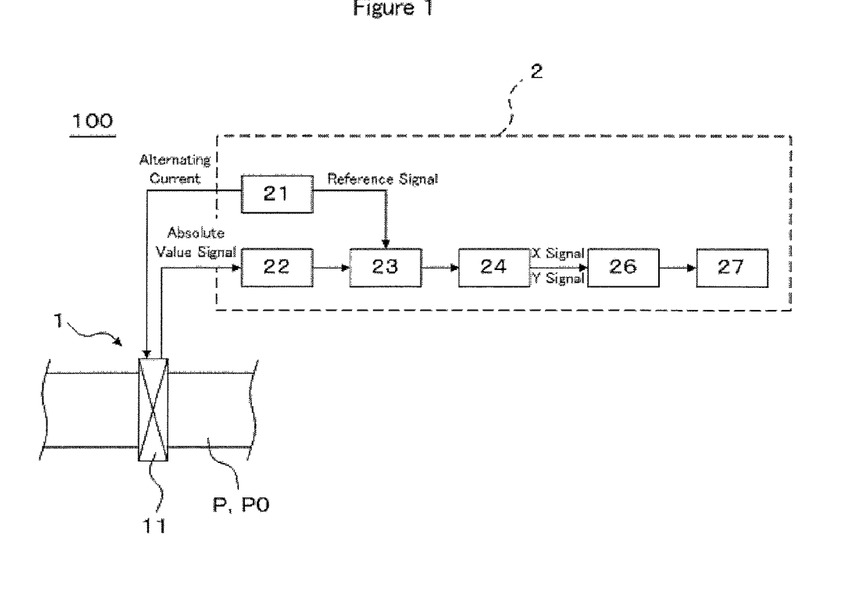
FIG. 1 is a schematic diagram to illustrate an outline configuration of an eddy current test apparatus to be used for a carburization sensing method relating to a first embodiment of the present invention.

FIG. 1 is a schematic diagram to illustrate an outline configuration of an eddy current test apparatus to be used for a carburization sensing method relating to a first embodiment of the present invention.

As shown in FIG. 1, an eddy current test apparatus 100 of the present embodiment includes a detection sensor 1 and a signal processing section 2.

The detection sensor 1 is configured to apply an alternating magnetic field to a steel tube P thereby inducing eddy current and detect the eddy current induced in the steel tube P. To be specific, the detection sensor 1 of the present embodiment includes an excitation coil that applies an alternating magnetic field to the inserted steel tube P, and a single detection coil 11 that detects the eddy current induced in the inserted steel tube P. The excitation coil and the detection coil 11 may be provided separately, or the detection coil 11 may combine the function of the excitation coil.

The signal processing section 2 is configured to pass an alternating current through the detection sensor 1 and sense whether carburization occurs or not in the steel tube P (on the inner surface of the steel tube P) based on a detection signal (an absolute value signal) outputted from the detection sensor 1. To be specific, the signal processing section 2 of the present embodiment includes an oscillator 21, an amplifier 22, a synchronous wave detector 23, a phase rotator 24, an A/D converter 26, and a determination section 27.

The oscillator 21 supplies a high frequency alternating current to the detection sensor 1 (specifically, the excitation coil of the detection sensor 1). This causes an alternating magnetic field to be applied to the steel tube P as described above, and eddy current is induced in the steel tube P.

An absolute value signal outputted from the detection sensor 1 (specifically, the detection coil 11 of the detection sensor 1) is amplified by the amplifier 22 and thereafter outputted to the synchronous wave detector 23.

The synchronous wave detector 23 performs synchronous wave detection of the output signal of the amplifier 22 based on the reference signal outputted from the oscillator 21. To be specific, a first reference signal having the same frequency and the same phase as those of the alternating current to be supplied to the detection sensor 1, and a second reference signal of which phase is shifted by 90° from the phase of the first reference signal are outputted from the oscillator 21 to the synchronous wave detector 23. Then, the synchronous wave detector 23 separates and extracts a signal component (a first signal component) that is in phase with the phase of the first reference signal and a signal component (a second signal component) that is in phase with the phase of the second reference signal. The separated and extracted first and second signal components are outputted to the phase rotator 24, respectively.

The phase rotator 24 rotates (shifts) the phases of the first signal component and the second signal component outputted from the synchronous wave detector 23 by the same predetermined amount, and outputs the first signal component as an X signal and the second signal component as a Y signal to the A/D converter 26. It is noted that the X signal and the Y signal that are outputted from the phase rotator 24 correspond to components of a signal waveform projected to the X axis and the Y axis, respectively in an X-Y vector plane represented by two mutually orthogonal axes (the X axis and Y axis), where the signal waveform is so-called a Lissajous figure and used for flaw inspection (that is, an absolute value signal waveform (to be precise, an absolute value signal waveform after the amplification by the amplifier 22) of the detection sensor 1 represented by a polar coordinate (Z, θ) where Z is amplitude and θ is phase).

The A/D converter 26 performs A/D conversion of the output signal of the phase rotator 24 and outputs it to the determination section 27.

The determination section 27 senses whether carburization occurs or not on the inner surface of the steel tube P based on the output data of the A/D converter 26 (that is, digital data obtained through A/D conversion of X signal and Y signal. Hereafter, referred to as X signal data and Y signal data). To be specific, the determination section 27 of the present embodiment compares the inputted X signal data with a threshold value Th3 which is predetermined and stored as described below, and determines that carburization has occurred on the inner surface of the steel tube P if the X signal data exceeds the threshold value Th3, and that carburization has not occurred on the inner surface of the steel tube P if the X signal data is within the threshold value Th3.

Hereafter, the method for determining the above described threshold value Th3 will be described.

When determining the above described threshold value Th3, the first to the seventh procedures to be described below will be performed.

(1) First Procedure

A material that has equivalent electromagnetic properties to those of the steel tube P (the base metal of the steel tube P) which is the test material and is not carburized is selected as a reference material P0. To be specific, a steel tube having the same constituents and dimensions (outer diameter and inner diameter) in terms of design specification as those of the test material is selected as the reference material P0. Then, at least three magnetic materials each having a different magnetic strength are attached to a target surface for carburization sensing (the inner surface in the present embodiment) of the reference material P0.

Figure 2:
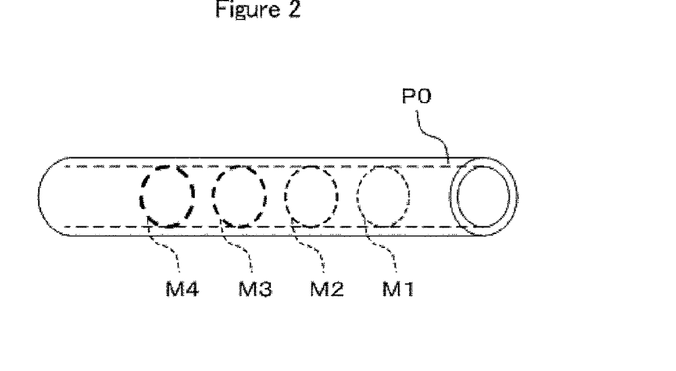
FIG. 2 is a schematic diagram to illustrate the outline of an example of a reference material to which magnetic materials are attached.

FIG. 2 is a schematic diagram to illustrate the outline of an example of a reference material P0 to which magnetic materials are attached. In the example shown in FIG. 2, magnetic tapes M1 to M4 each having a different number of windings are used as the magnetic material. Each magnetic tape M1 to M4 is inserted into a different location on the inner surface of the reference material P0 and attached thereto.

(2) Second Procedure (2-1) Measurement of Magnetic Strength of Magnetic Material Next, the magnetic strength of each magnetic tape M1 to M4 that is attached to the reference material P0 in the first procedure is measured. To be specific, a ferrite meter is oppositely disposed to the outer surface of the reference material P0 corresponding to the part where each magnetic tape M1 to M4 is inserted and the magnetic strength (amount of ferrite) of each magnetic tape M1 to M4 is measured by the ferrite meter.

Table 1 shows an example of the result of measuring the magnetic strength of each magnetic tape M1 to M4 that is attached to the reference material P0 as described above. It is noted that in the example shown in Table 1, the magnetic strength is measured by using a ferrite meter which applies an alternating magnetic field of 10 Hz to the reference material P0.

TABLE 1

| Magnetic tape | Number of windings(T) | Magnetic strength(Fe %) |
| --- | --- | --- |
| M1 | 5 | 0.035 |
| M2 | 10 | 0.045 |
| M3 | 30 | 0.060 |
| M4 | 50 | 0.067 |

(2-2) Acquisition of Eddy Current Test Output Value of Magnetic Material

On the other hand, the above described eddy current test apparatus 100 is used to perform an eddy current test on the reference material P0 attached with magnetic tapes M1 to M4, and thereby eddy current test output values of each magnetic tape M1 to M4 are acquired. Hereafter, this procedure will be described with reference to FIGS. 1 and 3.

Figure 3:
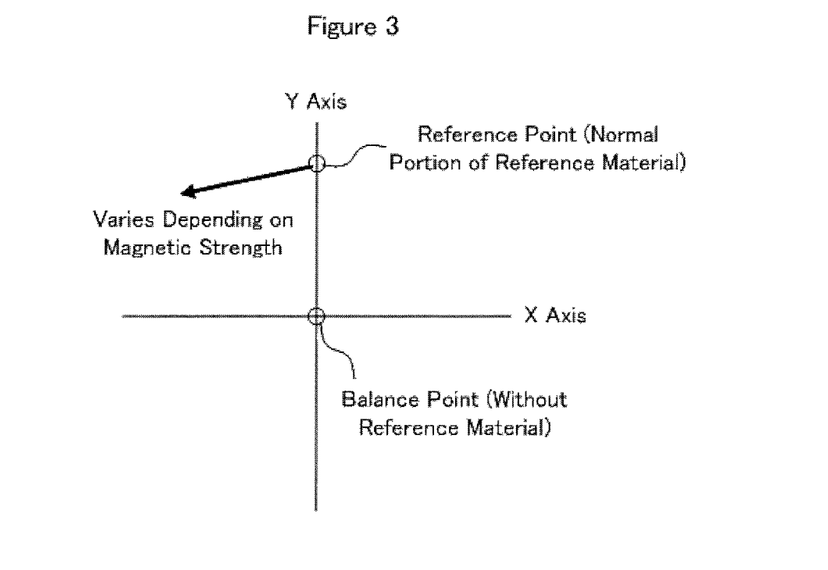
FIG. 3 is a schematic diagram to represent an X signal and Y signal outputted from the phase rotator, which is included in the eddy current test apparatus shown in FIG. 1, on an X-Y vector plane.

FIG. 3 is a schematic diagram to represent an X signal and Y signal outputted from the phase rotator 24, which is included in the eddy current test apparatus 100 shown in FIG. 1, on an X-Y vector plane.

When acquiring eddy current test output values of each magnetic tape M1 to M4, first, in a state in which the reference material P0 is not inserted into the detection sensor 1, the balancing quantity of a balance circuit (not shown) which is disposed in the preceding stage of the amplifier 22 is adjusted such that the X signal and the Y signal become zero (such that a spot corresponding to the front edge of a vector of which X axis component and Y axis component are the X signal and the Y signal, respectively is located at a balance point (an origin point) shown in FIG. 3) so that the first signal component and the second signal component, which are outputted from the synchronous wave detector 23, are zero, respectively.

Next, a part of the reference material P0 to which magnetic tapes M1 to M4 are not attached is inserted into the detection sensor 1 and halted thereat, and the amplification factor of the amplifier 22 and the phase rotation amount of the phase rotator 24 are adjusted such that the X signal is zero and the Y signal is a predetermined voltage (for example, 5V) (such that the front edge of a vector is located at the reference point shown in FIG. 3).

After the above described adjustment is performed in advance, the reference material P0 is moved in the axial direction such that each part of the reference material P0 to which the magnetic tapes M1 to M4 are attached is successively inserted into the detection sensor 1 and is successively halted with each part being inserted into the detection sensor 1, so that X signal data and Y signal data corresponding to each part are acquired. It is noted that as shown in FIG. 3, although the position of the front edge of the vector varies depending on the magnetic strength of each magnetic tape M1 to M4, the amount of variation is larger in the X axis direction than in the Y axis direction. For this reason, in the present embodiment, X signal data out of the X signal data and the Y signal data acquired as described above is used as the eddy current test output value of each magnetic tape M1 to M4.

(3) Third Procedure

Figure 4:
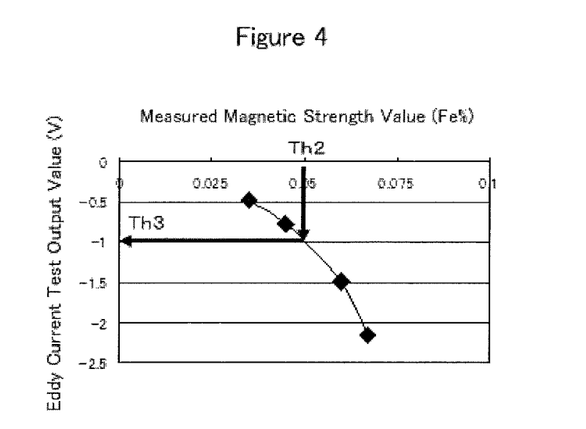
FIG. 4 shows an example of the correspondence between a measured magnetic strength value and an eddy current test output value, which is calculated in the first embodiment of the present invention.

Next, based on the measured magnetic strength values (see Table 1) and the eddy current test output values of each magnetic tape M1 to M4 obtained in the above described second procedure, a correspondence between the measured magnetic strength value and the eddy current test output value as shown in FIG. 4 is calculated. It is noted that the eddy current test output value of the example shown in FIG. 4 is a value obtained by performing an eddy current test by supplying an alternating current of 1 kHz to the detection sensor 1.

In the correspondence (see FIG. 4) between the measured magnetic strength value and the eddy current test output value, which is obtained by performing the first to the third procedures described above, although the eddy current test output value will be affected by the electromagnetic properties of the reference material P0 (the electromagnetic properties of the steel tube P which is the test material), the reference point thereof (see FIG. 3) stays substantially fixed.

(4) Fourth Procedure

On the other hand, the magnetic strength is measured on a plurality of carburized materials each having a different carburized depth. To be specific, a plurality of steel tubes (carburized materials) which are expected to have respectively different carburized depths on the inner surface are prepared. Then, similarly as in the case in which the magnetic strength of each magnetic tape M1 to M4 attached to the reference material P0 is measured in the above described second procedure, a ferrite meter is disposed oppositely to the outer surface of the carburized material and the magnetic strength (ferrite value) of each carburized material is measured by the ferrite meter. It is noted that, as the carburized material, it is preferable to select a steel tube which is identical in the dimensions (outer diameter and inner diameter) in terms of design specification to the reference material P0. Since this will facilitate the matching of the distance between the ferrite meter and the carburized material with the distance between the ferrite meter and the inner surface of the reference material P0 in the second procedure, the measurement condition for the magnetic strength in the second and the fourth procedures is more likely to be constant, and thus it is expected to achieve improved measurement accuracy.

Then, actual carburized depth of each carburized material is measured by cutting off each carburized material of which magnetic strength has been measured, and performing microstructure observation thereof.

Table 2 shows an example of the result of measuring the carburized depth and the magnetic strength of each carburized material as described above. It is noted that the magnetic strength shown in Table 2 is measured by using the same ferrite meter as used in the measurement of the example shown in Table 1 described above.

TABLE 2

| Carburized material | Carburized depth (µm) | Magnetic strength (Fe %) |
|---|---|---|
| No1 | 0 | 0.05 |
| No2 | 0 | 0.04 |
| No3 | 5 | 0.15 |
| No4 | 15 | 0.19 |

(5) Fifth Procedure

Figure 5:
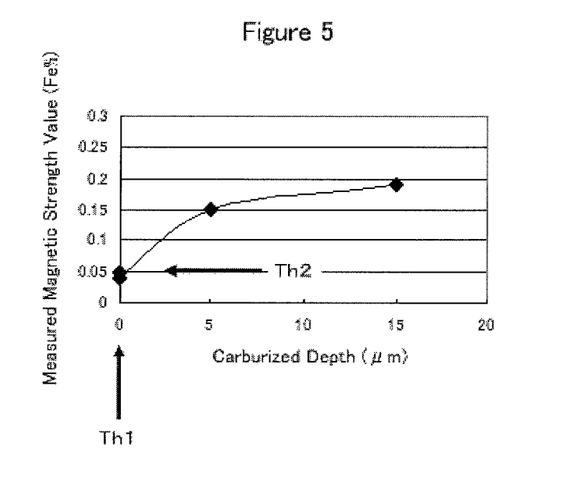
FIG. 5 shows an example of the correspondence between a carburized depth and a measured magnetic strength value, which is calculated in the first embodiment of the present invention.

Next, based on the carburized depths and the measured magnetic strength value of each carburized material (see Table 2) obtained in the above described fourth procedure, a correspondence between the carburized depth and the measured magnetic strength value as shown in FIG. 5 is calculated.

The correspondence (see FIG. 5) between the carburized depth and the measured magnetic strength value obtained by performing the above described fourth and fifth procedures is less likely to be affected by the electromagnetic properties of the base metal of each carburized material, and therefore by the electromagnetic properties of the steel tube P (the base metal of the steel tube P) which is the test material.

(6) Sixth Procedure

Next, based on the correspondence (see FIG. 5) between the carburized depth and the measured magnetic strength value obtained by the above described fifth procedure, a threshold value Th2 of the measured magnetic strength value corresponding to a threshold value Th1 of the carburized depth to be sensed is determined. In the example shown in FIG. 5, supposing that the threshold value Th1 of the carburized depth to be sensed is Th1=0 (µm), the threshold value Th2 of the measured magnetic strength value corresponding to this is given as Th2=0.05 (Fe %).

(7) Seventh Procedure

Lastly, based on correspondence between the measured magnetic strength value and the eddy current test output value (see FIG. 4) obtained in the above described third procedure, the threshold value Th3 of the eddy current test output value corresponding to the threshold value Th2 of the measured magnetic strength value determined in the sixth procedure is determined. In the example shown in FIG. 4, the threshold value Th3 of the eddy current test output value corresponding to the threshold value Th2=0.05 (Fe %) of the measured magnetic strength value determined as described above is given as Th3=−1 (V).

As described so far, the threshold value Th3 is determined and, as described above, is stored in the determination section 27 in advance.

It is noted that performing the sixth and the seventh procedures will result in that the threshold value Th3 of the eddy current test output value corresponding to the threshold value Th1 of the carburized depth to be sensed is determined, as in prior arts.

According to the method relating to the present embodiment, however, first in the sixth procedure, based on the correspondence between the carburized depth and the measured magnetic strength value as shown in FIG. 5, a threshold value Th2 of the measured magnetic strength value corresponding to a threshold value Th1 of the carburized depth to be sensed is determined. Since the correspondence between the carburized depth and the measured magnetic strength value as shown in FIG. 5 is not likely to be affected by the electromagnetic properties of the steel tube P, which is the test material, as described above, it is possible to accurately determine the threshold value Th2 of the measured magnetic strength value corresponding to the threshold value Th1 of the carburized depth to be sensed. Then, in the seventh procedure, based on the correspondence between the measured magnetic strength value and the eddy current test output value as shown in FIG. 4, a threshold value Th3 of the eddy current test output value corresponding to the threshold value Th2 of the measured magnetic strength value is determined. In the correspondence between the measured magnetic strength value and the eddy current test output value as shown in FIG. 4, although the eddy current test output value is affected by the electromagnetic properties of the steel tube P which is the test material as described above, since the reference point thereof stays substantially fixed, it is possible to accurately determine the threshold value Th3 of the eddy current test output value corresponding to the threshold value Th2 of the measured magnetic strength value.

Therefore, in the method relating to the present embodiment, by performing the sixth and the seventh procedures, it is possible, in contrast to prior arts, to accurately determine the threshold value Th3 of the eddy current test output value corresponding to the threshold value Th1 of the carburized depth to be sensed.

The determination section 27 compares the eddy current test output value (X signal data) which is inputted from the A/D converter 26 with the threshold value Th3, and if the eddy current test output value exceeds the threshold value Th3 (if it is less than −1 V in the example shown in FIG. 4), determines that a carburization has occurred on the inner surface of the steel tube P. On the other hand, if the eddy current test output value is within the threshold value Th3 (if it is not less than −1 V in the example shown in FIG. 4), the determination section 27 determines that carburization has not occurred on the inner surface of the steel tube P. As described above, in the method relating to the present embodiment, since the threshold value Th3 of the eddy current test output value which serves as the criterion for determining whether carburization occurs or not is determined more accurately than in prior arts, it is possible to accurately sense whether carburization occurs or not.

Figure 6:
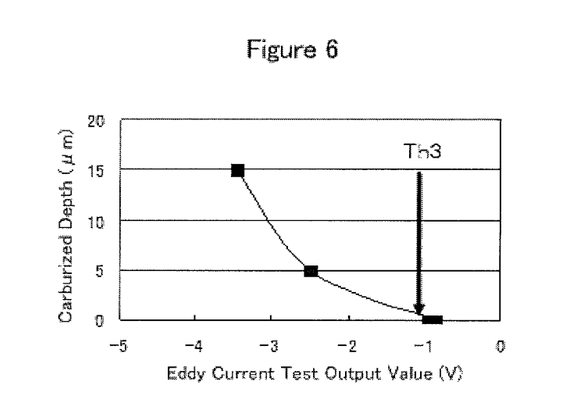
FIG. 6 shows an example of the result of sensing whether carburization occurs or not by a carburization sensing method relating to the first embodiment of the present invention.

FIG. 6 shows an example of the result of sensing whether carburization occurs or not of the steel tube P which is the test material by using the threshold value Th3 that is determined as described above. As shown in FIG. 6, it is seen that by using the threshold value Th3 as the determination criterion, it is possible to accurately sense whether carburization occurs or not.

<Second Embodiment>

In the carburization sensing method relating to the present embodiment, the configuration of the eddy current test apparatus to be used is different from that of the first embodiment. Because of this, although the procedure of acquiring the eddy current test output value of the magnetic material is different from that of the first embodiment, other procedures are the same as those of the first embodiment. Hereafter, description will focus on points different from the first embodiment.

Figure 7:
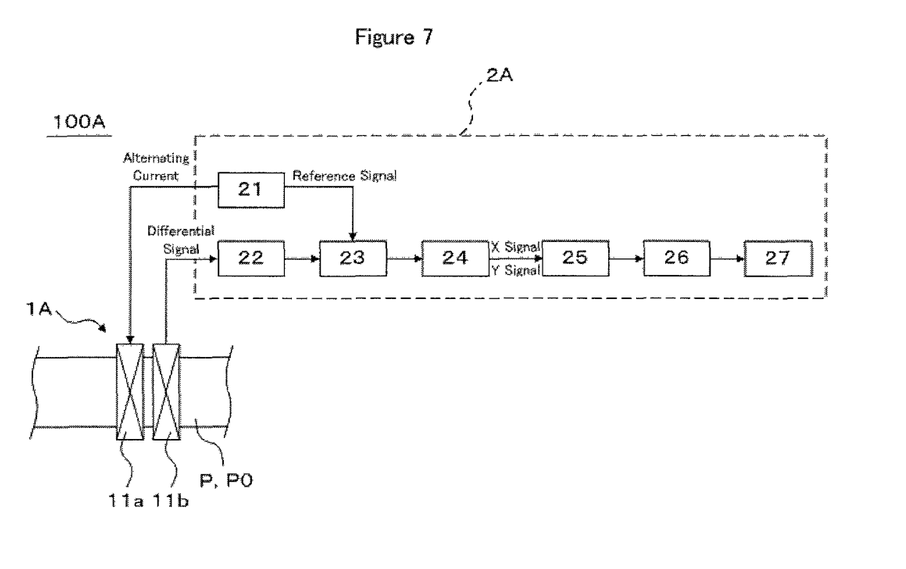
FIG. 7 is a schematic diagram to illustrate the outline configuration of an eddy current test apparatus to be used in the carburization sensing method relating to the second embodiment of the present invention.

FIG. 7 is a schematic diagram to illustrate the outline configuration of an eddy current test apparatus to be used in the carburization sensing method relating to the second embodiment of the present invention.

As shown in FIG. 7, the eddy current test apparatus 100A of the present embodiment also includes a detection sensor 1A and a signal processing section 2A, as with the eddy current test apparatus 100 of the first embodiment.

The detection sensor 1A of the present embodiment is also configured to induce eddy current by applying an alternating magnetic field to the steel tube P and to detect the eddy current induced in the steel tube P. However, a specific configuration of the detection sensor 1A is different from the detection sensor 1 of the first embodiment. The detection sensor 1A of the present embodiment includes an excitation coil that applies an alternating magnetic field to the steel tube P inserted therethrough, and a pair of detection coils 11a and 11b that detect the eddy current induced in the steel tube P that is inserted therethrough. The detection sensor 1A is configured to output a difference between detection signals at each detection coils 11a and 11b (a differential signal). The excitation coil and detection coils 11a and 11b may be provided as separate bodies, or the detection coils 11a and 11b may combine the function of the excitation coil.

The signal processing section 2A is configured to pass an alternating current through the detection sensor 1A and sense whether carburization occurs or not in the steel tube P (on the inner surface of the steel tube P). To be specific, the signal processing section 2A of the present embodiment includes a high-pass filter 25 that removes predetermined low frequency components from an X signal and a Y signal outputted from the phase rotator 24, and outputs them to an A/D converter 26. Since the signal processing section 2A of the present embodiment has the same configuration as that of the signal processing section 2 of the first embodiment excepting that it includes the high-pass filter 25, detailed description thereof will be omitted herein.

The determination section 27, which is included in the signal processing section 2A of the present embodiment, as well compares the X signal data inputted from the A/D converter 26 with the threshold value Th3 that is predetermined and stored, and if the X signal data exceeds the threshold value Th3, it determines that carburization has occurred on the inner surface of the steel tube P, and if the X signal data is within the threshold value Th3, it determines that carburization has not occurred on the inner surface of the steel tube P.

Hereafter, the method for determining threshold value Th3 in the present embodiment will be described.

The point where when determining the above described threshold value Th3, the above described first procedure (the procedure of attaching magnetic tapes M1 to M4 to a reference material P0) is performed is the same as in the first embodiment. Moreover, in the above described second procedure, the point where the procedure of measuring the magnetic strength of each magnetic tape M1 to M4 attached to the reference material P0 by a ferrite meter is performed is the same as in the first embodiment. By performing the above described procedures, it is possible to obtain the result as shown in Table 1 described above.

In the present embodiment, however, the content of the procedure of acquiring the eddy current test output value of each magnetic tape M1 to M4 attached to the reference material P0 in the above described second procedure is different from that of the first embodiment. Hereafter, this different procedure will be described with reference to FIGS. 7 and 8.

Figure 8:
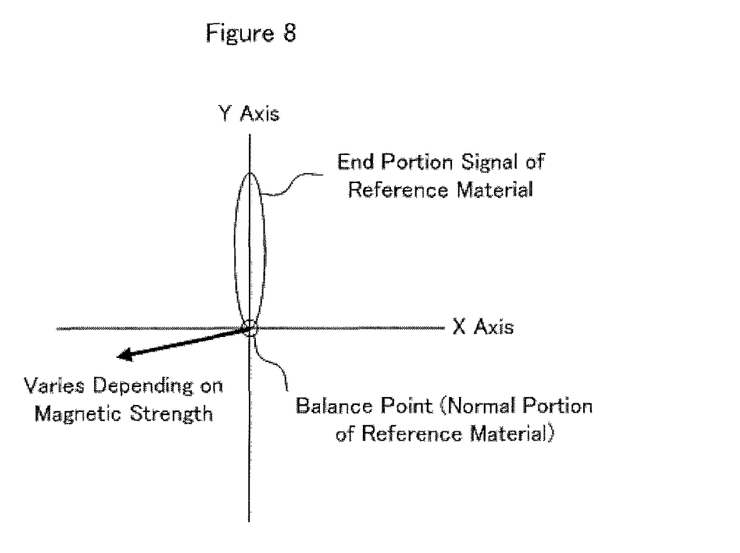
FIG. 8 is a schematic diagram in which an X signal and a Y signal outputted from the phase rotator, which is included in the eddy current test apparatus shown in FIG. 7, are represented on an X-Y vector plane.

FIG. 8 is a schematic diagram in which an X signal and a Y signal outputted from the phase rotator 24, which is included in the eddy current test apparatus 100A shown in FIG. 7, are represented on an X-Y vector plane.

When acquiring eddy current test output values of each magnetic tape M1 to M4, first, the reference material P0 is halted in a state where a part of the reference material P0 to which the magnetic tapes M1 to M4 are not attached is being inserted both through the detection coils 11a and 11b of the detection sensor 1, and the balancing quantity of a balance circuit (not shown) disposed in the preceding stage of the amplifier 22 is adjusted such that the X signal and the Y signal become zero (such that a spot corresponding to the front edge of a vector of which X axis component and Y axis component are the X signal and the Y signal, respectively is located at a balance point (an origin point) shown in FIG. 8) so that the first signal component and the second signal component, which are outputted from the synchronous wave detector 23, are zero, respectively.

Next, after the reference material P0 is drawn out from the detection coils 11a and 11b, the reference material P0 is moved in the axial direction again, and the amplification factor of the amplifier 22 and the phase rotation amount of the phase rotator 24 are adjusted such that a signal waveform (an end portion signal shown in FIG. 8), which is a locus of the spot obtained when the end of the reference material P0 successively passes through the detection coils 11a and 11b, is substantially symmetrical with respect to the Y axis, and the Y axis component becomes a predetermined voltage (for example, 5 V).

After performing the above described adjustment in advance, the reference material P0 is moved in the axial direction such that each part of the reference material P0 to which the magnetic tapes M1 to M4 are attached is successively inserted into the detection sensor 1 to acquire X signal data and Y signal data corresponding to each part. It is noted that as shown in FIG. 8, although the front edge position of a vector varies with a balance point being as a reference point depending on the magnetic strength of each magnetic tape M1 to M4, the amount of variation is larger in the X axis direction than in the Y axis direction. For this reason, in the present embodiment as well, out of the X signal data and the Y signal data which are acquired as described above, the X signal data is used as the eddy current test output value of each magnetic tape M1 to M4.

Figure 9:
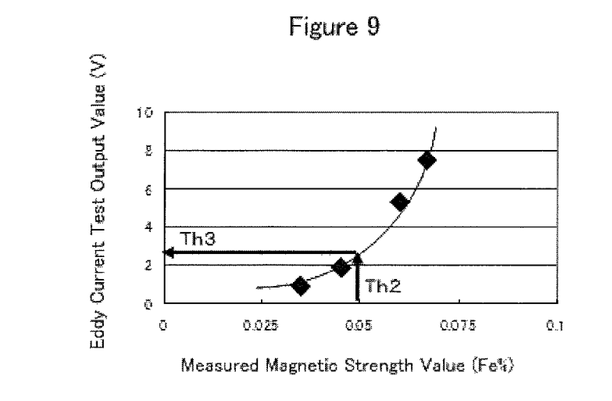
FIG. 9 shows an example of the correspondence between the measured magnetic strength value and the eddy current test output value which are calculated in the second embodiment of the present invention.

The point where after the procedure of acquiring the eddy current test output value of each magnetic tape M1 to M4 attached to the reference material P0 is performed as described above, the above described third procedure (the procedure of calculating the correspondence between the measured magnetic strength value and the eddy current test output value) is performed is the same as in the first embodiment. FIG. 9 shows an example of the correspondence between the measured magnetic strength value and the eddy current test output value which are calculated in the present embodiment. It is noted that the eddy current test output value shown in FIG. 9 is the value obtained by performing the eddy current test by supplying an alternating current of 10 kHz to the detection sensor 1A.

The point where when determining the threshold value Th3 of the present embodiment, besides the procedures as described above, the above described fourth procedure (the procedure of measuring the magnetic strength on a plurality of carburized materials), the fifth procedure (the procedure of calculating the correspondence between the carburized depth and the measured magnetic strength value), the sixth procedure (the procedure of determining the threshold value Th2 of the measured magnetic strength value corresponding to the threshold value Th1 of the carburized depth to be sensed), and the seventh procedure (the procedure of determining the threshold value Th3 of the eddy current test output value corresponding to threshold value Th2 of the measured magnetic strength value) are performed is the same as in the first embodiment. In the example shown in FIG. 9, the threshold value Th3 of the eddy current test output value corresponding to the threshold value Th2 of the measured magnetic strength value Th2=0.05% (Fe %) is given as Th3=2.5 (V).

Figure 10:
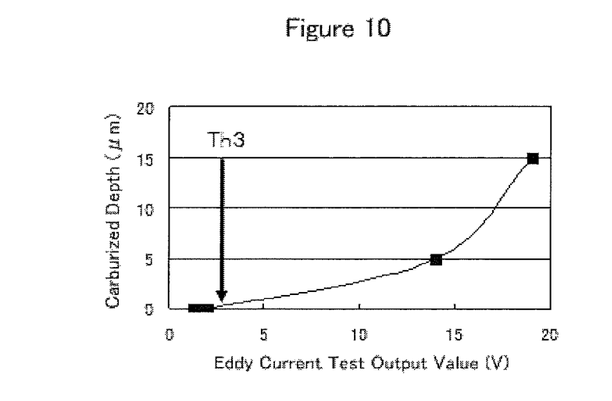
FIG. 10 shows an example of the result of sensing whether carburization occurs or not by a carburization sensing method relating to the second embodiment of the present invention.

FIG. 10 shows an example of the result of sensing whether carburization occurs or not of a steel tube P which is the test material by using the threshold value Th3 obtained as described above. It is revealed as shown in FIG. 10 that by using the threshold value Th3 as the determination criterion, it is possible to accurately sense whether carburization occurs or not.

The invention claimed is:

1. A method for sensing whether carburization occurs or not in a test material by an electromagnetic test, the carburization sensing method comprising:
   a first procedure of selecting a material that has equivalent electromagnetic properties to those of a test material and is not carburized as a reference material, and attaching at least three magnetic materials each having a different magnetic strength to a target surface for carburization sensing of the reference material;
   a second procedure of measuring magnetic strength of each magnetic material, which is attached to the reference material in the first procedure, and performing an electromagnetic test on the each magnetic material to acquire an output value thereof;
   a third procedure of calculating, based on the measured magnetic strength values and the electromagnetic test output values of the each magnetic material, which are obtained in the second procedure, a correspondence between the measured magnetic strength values and the electromagnetic test output value;
   a fourth procedure of measuring the magnetic strength on a plurality of carburized materials each having a different carburized depth;
   a fifth procedure of calculating, based on the carburized depths and the measured magnetic strength values of the each carburized material which are obtained in the fourth procedure, a correspondence between the carburized depth and the measured magnetic strength value;
   a sixth procedure of determining, based on the correspondence between the carburized depth and the measured magnetic strength value obtained in the fifth procedure, a threshold value of the measured magnetic strength value corresponding to a threshold value of a carburized depth to be sensed;
   a seventh procedure of determining, based on the correspondence between the measured magnetic strength value and the electromagnetic test output value obtained in the third procedure, a threshold value of the electromagnetic test output value corresponding to the threshold value of the measured magnetic strength value determined in the sixth procedure; and
   an eighth procedure of sensing whether carburization occurs or not in the test material based on a magnitude correlation between the electromagnetic test output value obtained by performing electromagnetic test on the test material, and the threshold value of the electromagnetic test output value determined in the seventh procedure.

2. The carburization sensing method according to claim 1, wherein
in the first procedure, any one of a magnetic tape, a ferrite core, and a specimen of a magnetic metal material is attached to the reference material as the magnetic material.

3. The carburization sensing method according to claim 2, wherein
in the second procedure and the eighth procedure, an electromagnetic test is performed using a sensor that outputs an absolute value signal or a sensor that outputs a differential signal.

4. The carburization sensing method according to claim 1, wherein
in the second procedure and the eighth procedure, an electromagnetic test is performed using a sensor that outputs an absolute value signal or a sensor that outputs a differential signal.

* * * * *